United States Patent [19]

Naylor

[11] Patent Number: 4,683,441

[45] Date of Patent: Jul. 28, 1987

[54] APPARATUS FOR ESTABLISHING THE DIFFERENCES BETWEEN MULTIPLE PAIRS OF ANALOG INPUT SIGNALS

[75] Inventor: Thomas K. Naylor, Belmont, Mass.

[73] Assignee: Siemens Aktiengesellschaft, Berlin and Munich, Fed. Rep. of Germany

[21] Appl. No.: 799,621

[22] Filed: Nov. 19, 1985

[51] Int. Cl.$^4$ .............................................. H03F 3/45
[52] U.S. Cl. ..................................... 330/69; 128/696; 128/902; 330/84; 330/107; 330/124 R; 330/147; 330/148
[58] Field of Search ................... 330/69, 84, 107, 108, 330/124 R, 147, 148, 252, 295; 128/695, 696, 709, 902

[56] References Cited

U.S. PATENT DOCUMENTS

| 4,152,659 | 5/1979 | Gordon | 330/84 X |
| 4,480,229 | 10/1984 | Van Kessel et al. | 330/84 |

OTHER PUBLICATIONS

Hadley, "Isolation Amplifier", *Wireless World*, vol. 87, No. 1545, Jun. 1981, p. 67.

*Primary Examiner*—James B. Mullins
*Attorney, Agent, or Firm*—David W. Gomes

[57] ABSTRACT

A bank of differential amplifier circuits includes specialized circuits to provide multi-channel differencing with a minimum number of active devices such that the differences between pairs of analog input signals, such as available from patient monitoring electrodes, are derived with half the number of active devices normally utilized. In one embodiment, two operational amplifier circuits are used in a differencing channel which functions together to provide differencing, a properly delayed input signal for use in another differencing channel, high input impedance buffering, a low impedance output for each differential amplifier channel, time-coincident, matched outputs for each differential amplifier channel, and with an additional operational amplifier, a DC rejection circuit which does not affect the low output impedance or the differencing function, thereby to eliminate the necessity of providing separate buffers and active delay circuits which can result in the use of twice the number of active devices. The above results are accomplished through the use of a predetermined ratio for the input and feedback resistors associated with the pairs of operational amplifiers in each channel and by tapping off a signal in one channel for use as an input signal in another channel.

19 Claims, 7 Drawing Figures

APPARATUS FOR ESTABLISHING THE DIFFERENCES BETWEEN MULTIPLE PAIRS OF ANALOG INPUT SIGNALS

FIELD OF INVENTION

This invention relates to signal processing, and more particularly, to the provision of a bank of differential amplifying circuits having high input impedances and low output impedances in which each differential amplifier circuit serves not only as a differential amplifier but also as a buffer and as a source of a properly delayed input signal for use in another differential amplifier circuit, thus reducing the number of active components necessary to provide the appropriate output signals.

BACKGROUND OF THE INVENTION

In order to provide for the processing of analog signals so as to derive the differences between two signals, it is oftentimes necessary to adjust the phase or time relationship between the signals at the input terminals of a differential amplifier so that the signals arrive in phase or in time-coincidence, such that an appropriate difference signal can be derived. It is common practice in instrumentation amplifiers to use two identical or balanced preamplifiers preceding a differential amplifier.

To provide for the appropriate phase change for signals that have become somewhat out of phase as is the case when certain of the analog signals are amplified, it is common practice to provide additional buffering stages which include active devices so as to alter the phase of the input signal, thereby to precondition the input signal so that it may be appropriately phased with another input signal which is also delayed. Moreover, such circuits usually must be provided with high input impedances through buffering and low output impedances to permit further signal processing.

Nowhere is this more important than in the area of patient monitoring through electrocardiograms, in which numerous electrical signals derived from electrical contacts or electrodes located on the patient body are to be subtracted one from the other. While the subject system will be described in connection with such patient monitoring circuits, its ability to reduce the number of active components in any bank of differencing circuits permits use of the subject circuit in virtually any case in which there are multiple pairs of signals and in which one signal of a pair is to be combined with or subtracted from another signal of the pair.

For purposes of illustration, in patient monitoring, it is standard that body-carried electrodes provide analog signals corresponding to those sensed at the left arm (LA), the right arm (RA), the left leg (LL), the right leg (RL) and the chest (C). As will be appreciated, the chest position may be at one of several locations. The electrical signals which are utilized by patient monitoring instruments are the difference signals determined by pairs of the above-mentioned electrical signals, with standard pair groupings being as follows:

I (LA-RA)
II (LL-RA)
III (LL-LA)

These difference signals are most easily derived by analog circuitry coupled directly to receive the electrode signals.

In one typical application, there may be as many as four differential amplifiers which are connected via buffers to the four input signals LA, RA, LL and C. A further signal, RL, which refers to the signal derived from the right leg, is also utilized as a ground or neutral return. For such a system, the four differential amplifiers typically include three active devices, operational amplifiers, whereas the buffers each include at least one operational amplifier. In such a four-channel system, sixteen such active devices are utilized, which is both costly in terms of the cost of the final device, including its large, isolated power supplies, and costly also in terms of the amount of "real estate" utilized on a printed circuit board.

As will be described, the subject circuit utilizes only half the number of active devices of the prior art circuits. Thus, in the interest of being able to provide patient monitoring instrumentation with increased capability for multiple input signals, significant improvements can be afforded by reducing the number of active components in the signal conditioning circuitry. The problem is to reduce the number of active components without altering the high input impedance characteristics provided by the buffers, while at the same time permitting the filtering out of DC components without altering the low impedance output characteristic of the differential amplifiers. Moreover, it is important that all this be done while still providing output signals, which are both time-coincident and magnitude-adjusted to permit further signal processing.

The ability to accommodate multiple analog input signals with a minimum of component parts enables the production of compact instrumentation capable of simultaneously monitoring more patient parameters, thus reducing the cost of patient monitoring instrumentation needed for a given performance level beyond the cost savings afforded by the simple reduction of components. Less power is required, so the components operate cooly and last longer. Of course, for battery-operated units, it is important to reduce the overall power consumption of the circuits to increase longevity with a given battery charge. Thus, a reduction of active components not only permits less costly instrumentation, it also permits increased longevity or, concomitantly, an increased number of monitorable parameters.

SUMMARY OF THE INVENTION

Accordingly, circuitry is provided by the present invention which uses fewer active components to calculate standard difference signals, whether used by patient monitoring apparatus or not. To this end, a bank of differential amplifier circuits having a minimum number of active devices is provided for establishing the differences between time-coincident pairs of analog input signals, such as available from patient monitoring electrodes, with a reduction in the number of active devices utlized being accomplished through the use of specialized differential amplifier circuits, each of which simultaneously serves multiple functions of providing differencing, high input impedance buffering, a source of a properly delayed input signal for another differencing channel, a low impedance output for each differential amplifier channel, time-coincident, matched outputs for each differential amplifier channel, and a DC rejection circuit which does not affect the low output impedance or the differencing function, thereby to eliminate the necessity of providing separate buffers and active delay devices.

In order to accomplish this, each differential amplifier circuit includes two operational amplifiers, each having input and feedback resistors with a predetermined ratio of values. More particularly, the ratio of the feedback resistor to the input resistor of the first operational amplifier equals the ratio of the input resistor to the feedback resistor of the second operational amplifier. How this ratio of values provides for the unique functioning of the entire circuitry will be described below.

First, it should be noted that one operational amplifier of the pair provides the differential amplifier function, while both operational amplifiers serve as high impedance buffers. Secondly, the feedback point for the second operational amplifier of the pair provides a properly delayed input signal for another operational amplifier in a different differential amplifier circuit. This eliminates the necessity of using additional active components to provide buffering or to provide appropriately delayed, time-coincident input signals for the differential amplifiers. The above-mentioned resistor ratio values assure differential amplifier output signals which are time-coincident and which are multiplied by the same constant to permit further processing without additional signal conditioning.

When patient monitoring is involved, tapping selected signals from additional attenuators provides signals which can be summed to form a Wilson summing junction. The above-mentioned resistor ratios also permit the use of an operational amplifier integrator to filter out DC components without altering the low output impedance characteristic of the differential amplifier and without affecting the differencing function.

In this system, not only do the differential amplifiers produce signals which are utilized for other differential amplifiers, the provision of appropriately delayed output signals provides for uncomplicated subsequent processing, since the output signals from the subject circuit are all appropriately time-coincident. Importantly, separate buffer stages are eliminated, with a portion of each differential amplifier circuit providing the buffering function.

As mentioned above, in order to accomplish this, the differential amplifier circuits are comprised, in a preferred embodiment, of only two active devices, i.e., only two operational amplifiers. The first operational amplifier of the pair is configured to be an unbalanced differential amplifier. The second operational amplifier of the pair is provided with a passive circuit comprising a voltage dividing feedback circuit to develop a delayed signal for use as an appropriately delayed input signal for the first operational amplifier of a different differential amplifier. The special ratio of the values of the passive components provides for appropriately delayed input signals, for amplitude-adjusted difference signal outputs and for the ability to utilize operational amplifier integrators for filtering out DC components.

Moreover, with respect to patient monitoring, appropriately time-coincident signals are derivable from the outputs of the differential amplifier circuits through the use of attenuators with resistors having the above ratio of values to permit a socalled Wilson summing junction for patient monitoring purposes. The Wilson summing junction is one in which a reference voltage is derived from the summation of the LA, RA and LL input signals and combined with the chest input to serve as another indication of heart condition. This requires only one additional differential amplifier in which one-third of the LA+RA+LL signal is subtracted from the chest electrode signal, C.

In summary, not only are the differential amplifying circuits utilized to provide the appropriate difference signals required for the multiple analog inputs, signals are derivable from portions of these circuits which may be utilized as input signals to different differential amplifier circuits which are appropriately time-conincident with other input signals to these circuits. Dedicated high-impedance buffering stages are completely eliminated, therefore, not only reducing the active component part count, but also the cost thereof. Because of the configuration of the differential amplifier circuits, their passive components and, more particularly, the values of these passive circuits, it is possible to filter out DC components with a standard operational amplifier integrator, since the input of the integrator at DC corresponds to the virtual ground of the system.

Finally, the subject circuits, with or without DC being filtered, provide low impedance output signals which may be utilized in follow-on processing circuitry not only because of their low impedance, but also because of their time-coincidence, such that no further balancing, delaying or phase shifting are required.

BRIEF DESCRIPTION OF THE DRAWINGS

These and other features of the subject invention will be better understood in connection with the Detailed Description taken in conjunction with the Drawing of which.

DETAILED DESCRIPTION

Figure 1:
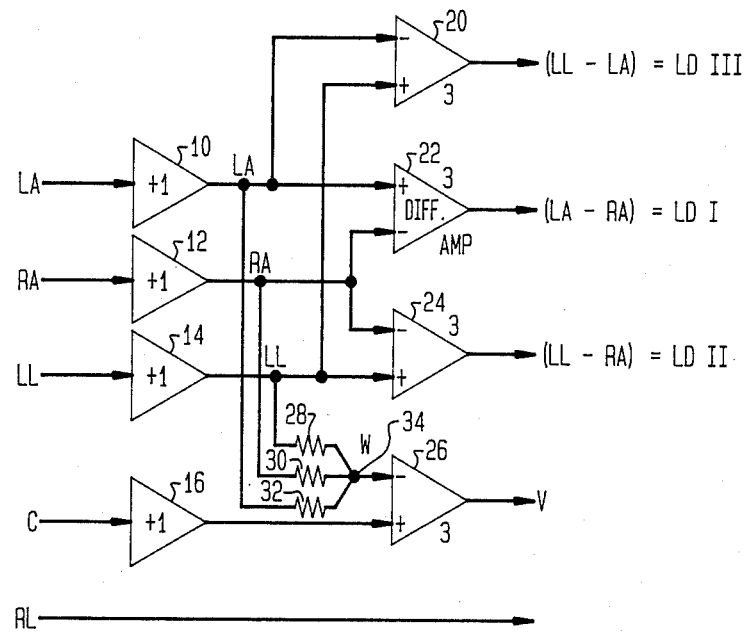
FIG. 1 is a schematic diagram of a prior art patient monitoring difference circuit illustrating the utilization of active buffering circuits to drive a number of passive components and complex differential amplifier assemblies used therein.

Referring now to FIG. 1, a typical patient monitoring system differencing circuit is depicted which accommodates five patient-mounted electrodes which produce analog input signals corresponding to voltage sensed at the left leg (LL), right leg (RL), left arm (LA), right arm (RA) and chest (C). This circuit produces signals representing the differences between selected pairs of these analog input signals. The above system utilizes a bank of buffer amplifiers 10–16 which are supplied respectively with the aforementioned LA, RA, LL and C input signals derived from the aforementioned electrodes. The outputs of the buffer circuits are provided to differential amplifiers diagrammatically illustrated at 20–26, with the amplifiers in the usual case having at least three active components therein, normally high gain operational amplifiers. The purpose of the buffers is to provide a high input impedance for the circuit, whereas the outputs of the differential amplifiers are low impedance outputs in order to permit further processing. When doing electrocardiograms, the output leads derive the following differences: LDI=(LA-RA); LDII=(LL-RA); and LDIII=(LL-LA).

Conventionally, there are four leads from the differential amplifier circuit labelled LDI, LDII, LDIII and V. In addition to the first three difference signals, there is the Wilson summing junction which sums the outputs of buffer amplifiers 10, 12 and 14, i.e., LA, RA and LL, through resistors 28, 30 and 32 to form a Wilson summing junction at node 34 which is applied to the inverting input of differential amplifier 26. The non-inverting input to differential amplifier 26 is provided with a signal derived from a chest electrode, such that a voltage V=(C-W) is provided which, when the chest electrode is moved about the patient's chest, provides further information to the cardiologist as to the relative functioning of the heart of a patient. The RL electrode is usually utilized to establish a ground or neutral return.

It will be appreciated that, assuming each differential amplifier in FIG. 1 has at least three active components, there are sixteen operational amplifiers utilized in the prior art circuit in order to derive the needed difference signals. The subject invention involves the reduction of the number of active devices in such a circuit which processes pairs of analog input signals, from whatever source. As will be seen hereinafter, the number of active devices in the circuit of FIG. 1 can be halved. The differential amplifier circuits in the subject invention include two operational amplifiers with the operational amplifiers serving as buffers as well as providing for differencing and for providing appropriately delayed input signals used elsewhere in the circuit.

Figure 2:
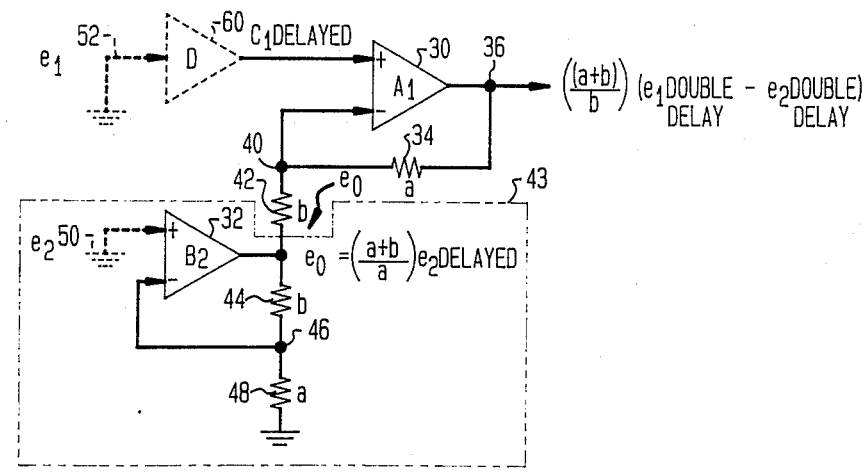
FIG. 2 is a schematic diagram illustrating a differential amplifier circuit for the processing of multiple analog input signals, the difference of which is to be derived, in which only two active components are utilized and in which the resistive components utilized are of such a value as to permit the derivation of a signal which is usable as an input signal to another differential amplifier for multiple differencing applications.

Referring now to FIG. 2, a schematic diagram is illustrated in which a differential amplifier circuit made according to the subject invention includes a pair of operational amplifiers 30 and 32, with the nomenclature adopted throughout being that the first of the pair is designated with a capital letter A. Amplifier 32, which is the second amplifier of the pair, is designated by the capital letter B.

OPERATION OF THE DIFFERENTIAL AMPLIFIER CIRCUIT

For the following analysis, it will be assumed that the operational amplifiers have infinite gain, although, in reality, the high gain amplifiers have a DC gain of $10^4$. The errors introduced by the fact that the amplifier gains are limited are not significant for the purpose of the present discussion. The high gain of the operational amplifier ensures that only a small difference in voltage at its inputs is needed to produce a reasonable output voltage. Hence, the voltage at its inverting input is forced to be approximately equal to the voltage at its non-inverting input.

It will be noted that a feedback path is established around amplifier 30 which includes a feedback resistor 34 having a value "a," with resistor 34 being connected between an output node 36 of amplifier 30 and the inverting input thereto. It will also be appreciated that the output node 38 of amplifier 32 is applied to a node 40 through an input resistor 42 having a value equal to "b" and that the feedback path to the second of the operational amplifiers has a feedback resistor 44 coupled between the output of amplifier 32 and its inverting input. A node 46 is established between resistor 44 and input resistor 48, with resistor 44 and resistor 48 forming an attenuator or voltage dividing circuit between node 38 and ground. The values of resistor 44 and 48 are respectively "b" and "a." In one embodiment, resistor 44=49,800 ohms, resistor 48=10,000 ohms, resistor 34=10,000 ohms and resistor 42=49,800 ohms, with the operational amplifiers being TL-072 manufactured by Texas Instruments. The values of "a" and "b" determine the gain of the amplifiers, with the gain of amplifier 30 being (a+b)/b and the gain of amplifier 32 being (a+b)/a.

It can be shown that, assuming an input signal $e_2$ is applied to the non-inverting input terminal of amplifier 32, the voltage at node 38, $e_o$, is equal to (a+b)/a ($e_2$ *delayed*). The delay is because of the propagation associated with amplifier 32. It will be appreciated that the output of amplifier 32 would be zero if the non-inverting input were grounded as shown at 50. Hence, with $e_2$ equal to zero, $e_0=0$ and amplifier 30 will have an output equal to (a+b)/b ($e_1$).

Note that the high input impedance non-inverting input terminal of operational amplifier 30 causes the amplifier 30 to drive the input node 40 to a voltage corresponding to $e_1$. Since input resistor 42 is a low impedance, the high impedance input node of amplifier 32 may be utilized so that the signal $e_2$ will see a high impedance, with the $e_0$ low impedance output of amplifier 32 being able to successfully drive the amplifier 30 so that amplifier 30 functions as an inverting amplifier. With $e_1$ and $e_2$ present, the output of amplifier 30 is proportional to the difference between $e_1$ and $e_2$.

To further analyze the circuit of FIG. 2, if the input point 38 to amplifier 30 were to be $e_0$, then it can be demonstrated that the output of amplifier 30 would contain an unwanted $e_1$ term instead of $e_1-e_o$. The following explains the derivation of the unwanted $e_1$ term and how it can be eliminated.

If $e_1$ to the non-inverting input to amplifier 30 is made to equal zero and $e_2$ is no longer grounded but now moves from zero, the resultant output of amplifier 30 will be the difference of the two signals, $e_1$ and $e_2$. If $e_1$ were grounded as illustrated at 52 and $e_2$ drives amplifier 32, the output of amplifier 32 will be the same as the input to amplifier 32, namely $e_2$ *delayed* times some constant, in this case (a+b)/a. Amplifier 32, therefore, applies a non-inverted delayed signal to node 40. The amplifier 30 inverts this signal at 36. With the gain of amplifier 30 being −a/b, moving its input results in an output −a/b($e_o$) if $e_1$ is held at zero potential.

However, with $e_2=0$, then $(a+b)/b$ $e_2$ delayed$=0$, and the output of amplifier 30 is $(a+b)/b$ $e_1$. If $e_o$ and $e_1$ are ungrounded and therefore applied at the same time by super-positioning, one can obtain the output from amplifier 30 to be $(a+b)/b$ $(e_1-a/b$ $e_o)$. The result is that the output is equal to $(e_1-a/b$ $e_o)$, which can be rewritten as $e_1+a/b(e_1-e_o)$. Thus, there is an unwanted term $e_1$ by itself which has nothing to do with the difference between $e_1$ and $e_o$. It will thus be appreciated that the differential amplifier 30 will not subtract $e_1$ from $e_o$ unless certain adjustments are made as follows.

In order to obtain the appropriate difference without the $e_1$ term, an amplifier circuit 43, including feedback and input resistors 44 and 48, is placed in the circuit of amplifier 32 to make the output of amplifier 32 equal to $(a+b)/a$ $(e_2)$. If this is accomplished, then the output of amplifier 32 equals $(a+b)/a$ $(e_2)$, and it can be shown that the output of amplifier 30 will be $(a+b)/b$ $(e_1-e_2)$. In this case, the difference $e_1-e_2$ is multiplied by $(a+b)/b$, which is a constant, and the solitary $e_1$ term is eliminated.

DEVELOPMENT OF TIME-COINCIDENT INPUT SIGNALS

All of the above discussion assumes that the inputs to amplifier 30 are time-coincident. In order for this to occur, since $e_2$ is delayed by amplifier 32, the normal practice would be to insert a buffer amplifier 60 to delay $e_1$ in order that the two signals $e_1$ and $e_2$ be properly differenced.

The $e_1$ $_{delayed}$ signal, rather than being produced through the use of a buffer, is derivable from the feedback node between the feedback and input resistors of another B operational amplifier, from whence comes the saving of at least one active device per difference channel. The other saving of at least one active device per difference channel comes from the use of only two operational amplifier per differential amplifier circuit instead of three.

Figure 3:
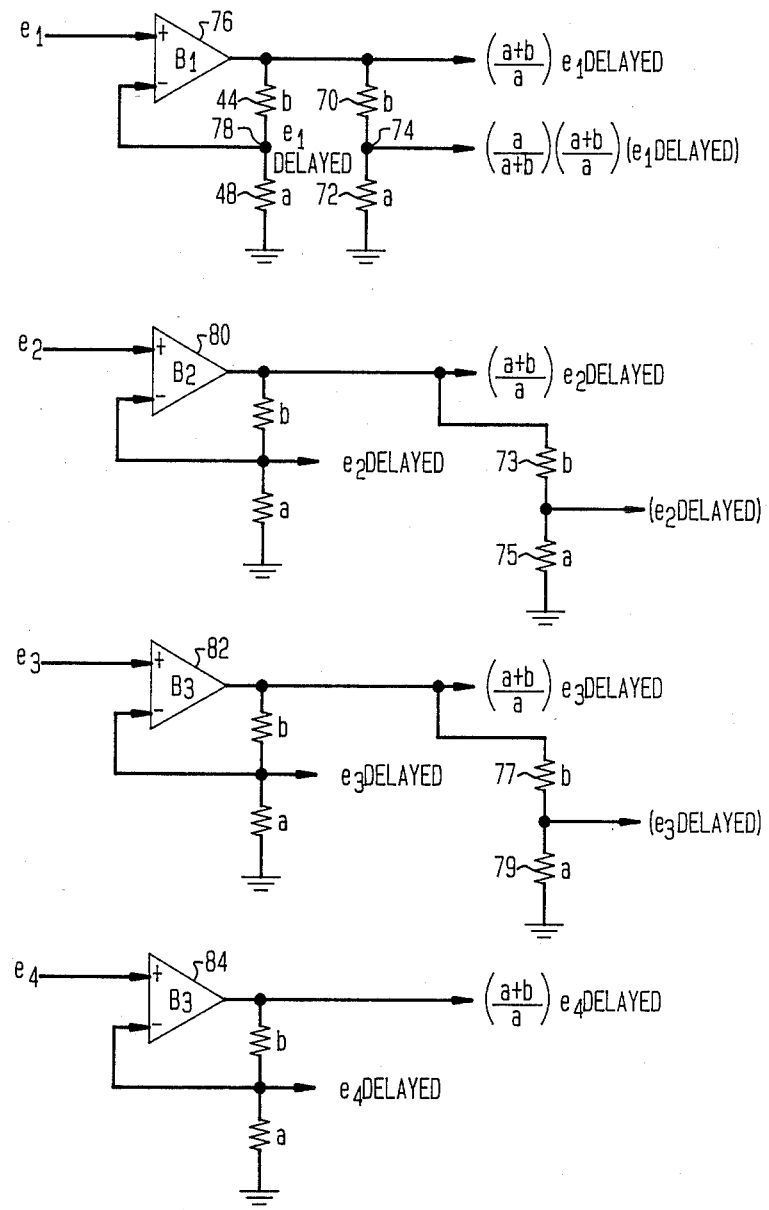
FIG. 3 is a series of schematic diagrams illustrating the outputs of the second operational amplifiers of a pair utilized in the subject differential amplification circuit, whereby the various delayed outputs are derived.

How $e_1$ $_{delayed}$ is obtained can be seen from FIG. 3. Through analysis of a voltage dividing circuit comprising resistors 70 and 72 connected in parallel with like-valued resistors 44 and 48, it can be shown that the signal at output node 74, $e_1$ $_{delayed}$, equals $[a/(b+a)]$ $[(a+b)/a]$ $e_1$ $_{delayed}=e_1$ $_{delayed}$. It can therefore be seen that such a circuit as is presented by either resistors 44 and 48 to 70 and 72 produce a node at which $e_1$ $_{delayed}$ is available. This being the case, with the removal of the circuit 70 and 72, the output at node at 78 is $e_1$ $_{delayed}$, with the output of amplifier $B_1$ being $(a+b)/a$ $e_1$ $_{delayed}$.

The purpose of the FIG. 3 diagram is to illustrate that for amplifiers B1, B2, B3 and B4, here illustrated at 76, 80, 82 and 84, respectively, the appropriate $e_1$ $_{delayed}$, $e_2$ $_{delayed}$, $e_3$ $_{delayed}$ and $e_4$ $_{delayed}$ signals are available to the high impedance, non-inverting inputs of the various B amplifiers, here illustrated at 76, 80, 82 and 84, respectively. Note that the addition of resistors 72 and 74 have little, if any, effect on the output of B since it is a low impedance output. The adding of attenuators 70, 72, 73, 75, 77 and 79 is necessary to develop the Wilson summing junction signal for patient monitoring, as will now be described in connection with FIG. 4.

PATIENT MONITORING

Figure 4:
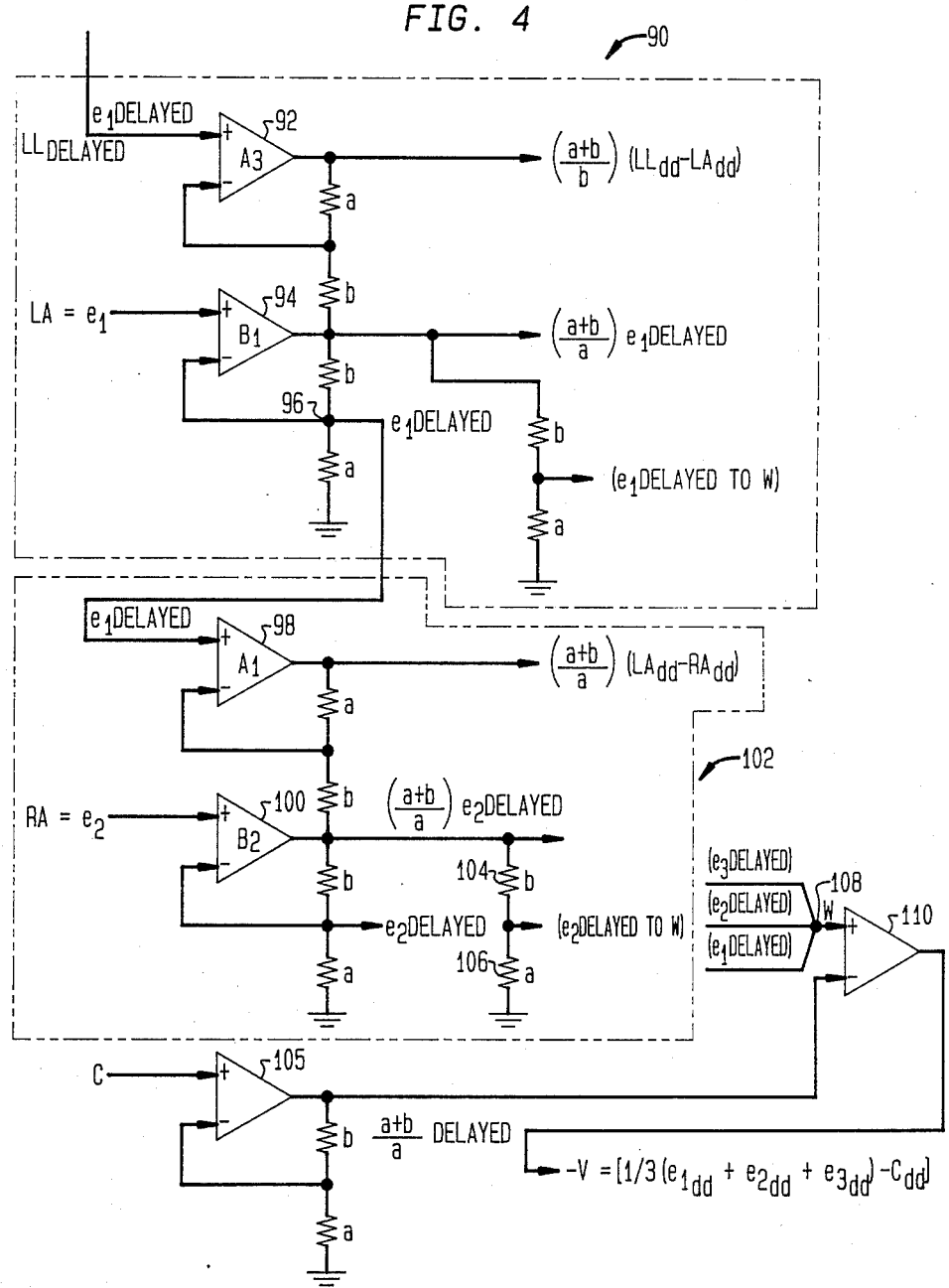
FIG. 4 is a schematic diagram illustrating, in a patient monitoring application, that the output of one of the differential amplifiers is usable as the input to another one of the differential amplifiers, also illustrating that the attenuated outputs of various nodes of predetermined differential amplifiers may be utilized directly to form a Wilson summing junction.

Referring to FIG. 4, in the case of patient monitoring, a differential amplifier circuit, here illustrated within dotted outline 90, has an amplifier 92, here illustrated at $A_3$, with a signal $e_3$ $_{delayed}$ being applied to its non-inverting input. Here, $e_3$ is defined as LL delayed. Amplifier 94, which is the second of the pair in this differential amplifier, is supplied with $LA=e_1$ such that an $e_1$ $_{delayed}$ signal is available at node 96. This is supplied to a second differential amplifier, with second differential amplifier including amplifier $A_1$ here illustrated at 98, which also includes a $B_2$ amplifier, here illustrated at 100. Note the $B_2$ amplifier is being shown as having an input signal $RA=e_2$. The resulting output of differential amplifier 102 is therefore $(a+b)/b$ $(LA_{dd}-RA_{dd})$, where "dd" stands for "double-delayed."

What can be seen from FIG. 4 is that for differential amplifier 102, an $e_1$ $_{delayed}$ signal from differential amplifier 90 can be supplied along with an $e_2$ undelayed signal, such that the appropriate difference signal $(a+b)/b$ $(LA_{dd}-RA_{dd})$ is available.

WILSON SUMMING JUNCTION

What will also be appreciated from FIG. 4 is that the $e_2$ $_{delayed}$ signal can be again generated by an identical voltage dividing network composed of resistors 104 and 106 so that, for instance, $e_1$ $_{delayed}$, $e_2$ $_{delayed}$ and $e_3$ $_{delayed}$ may be derived from these additional passive components and supplied to Wilson summing junction 108 applied to the non-inverting input of an operational amplifier 110, with the inverting input being supplied with the C signal applied to an operational amplifier 105, having feedback and input resistors "b" and "a" as illustrated. Thus, the signal applied to the inverting input to amplifier 110 is $(a+b)/a$ times $C_{delayed}$. The result is that the output voltage of amplifier 110, $-V$, equals $[\frac{1}{3}(e_1$ $_{dd}+e_2$ $_{dd}+e_3$ $_{dd})-C_{dd}]$. Note the time-coincidence of all voltages supplied to the Wilson summing junction. Thus, not only can various time-coincident difference signals be derived, but also $-V$ can be easily derived from time-coincident signals through the addition of passive circuit components 104 and 106 to the appropriate amplifiers.

Figure 5:
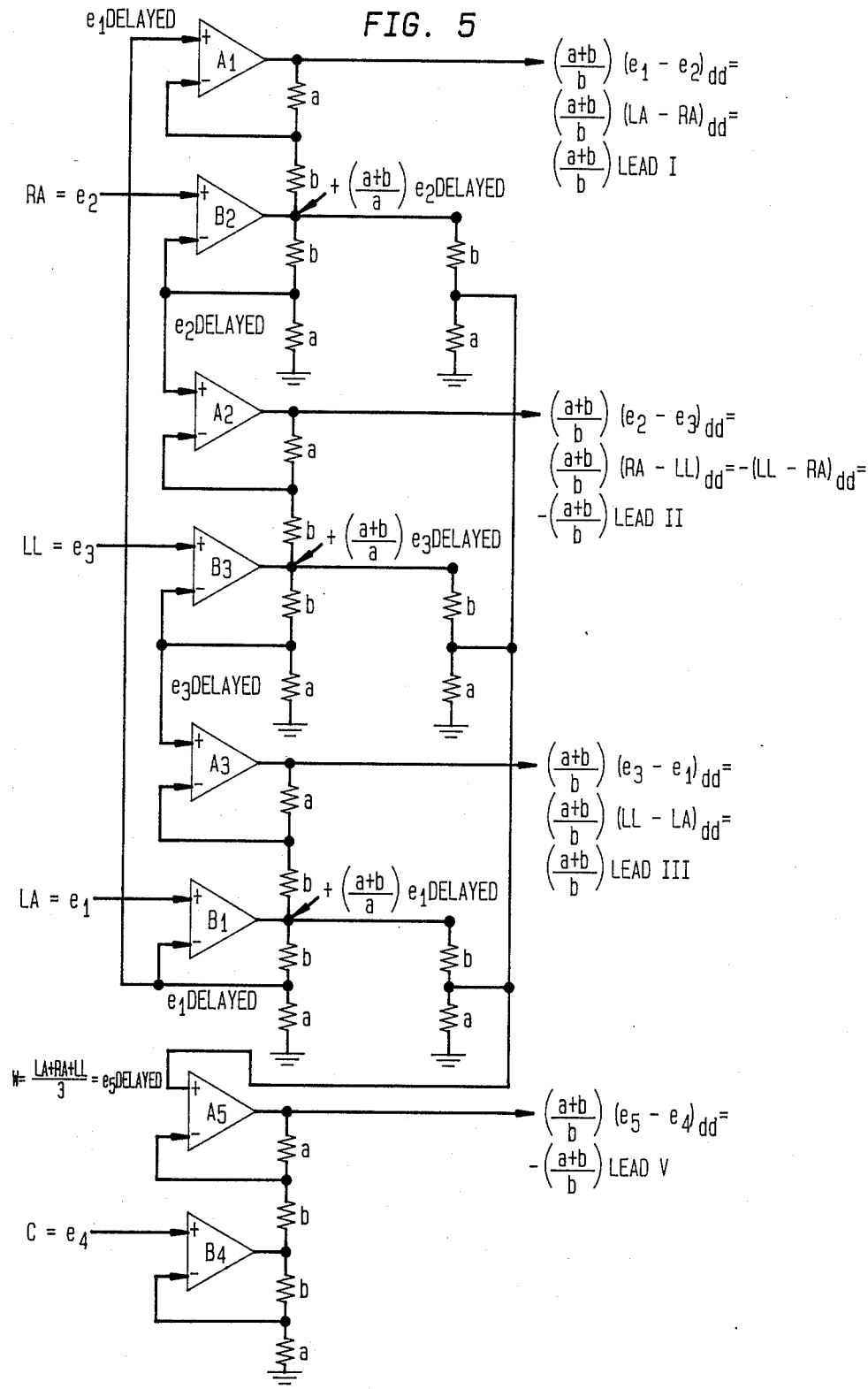
FIG. 5 is a detailed schematic diagram of the subject multiple differencing system utilized for the patient monitoring case, showing the utilization of various outputs of various nodes of each differential amplifier circuit as inputs to other differential amplifier circuits, thereby eliminating the necessity of providing further active circuitry to provide the appropriate inputs to the differential amplifier circuits; and, FIGS. 6A and 6B are respectively a prior art DC component rejection circuit and an integrator circuit involving the utilization of an operational amplifier connected between the output of a differential amplifier and a node corresponding to the ground reference of this amplifier, thereby to provide for a low impedance output signal having DC components filtered therefrom.

Referring to FIG. 5, a complete system for patient monitoring is illustrated. In this case, LA equals $e_1$, RA equals $e_2$, LL equals $e_2$, LL equals $e_3$, C equals $e_4$, and $e_5$ $_{delayed}$ equals W which equals $(LA+RA+LL)/3$. From inspection of this diagram and assuming matched amplifiers with infinite gain, then the LDI equals (LA-RA), which has been double-delayed with a constant $(a+b)/b$, with the LDII signal being a double-delayed $-(LL-RA)$, giving a $-LDII$ signal also with a $(a+b)/b$ constant, and with a LDIII signal being (LL-LA) also double-delayed with a $(a+b)/b$ constant. Finally, the $-V$ signal is the chest signal, subtracted from the traditional Wilson junction signal, also double-delayed and with a $(a+b)/b$ constant.

What will be immediately apparent is that the signals on all of the leads are double-delayed, and all of the signals are multiplied by the same constant. Thus, all the signals are time-coincident and multiplied by the same constant so that additional signal conditioning is unnecessary prior to further signal processing.

What will also be appreciated is that all of the input signals to the operational amplifiers are to the non-inverting inputs thereof, (e.g., high impedance nodes), whereas the outputs of all of the differential amplifiers are low impedance outputs capable of being utilized for downstream processing. The circuit shown thus far includes differential amplifiers, including an A amplifier and a B amplifier, with the B amplifiers of the group supplying the appropriate A amplifiers with an appropriately delayed signal. The B amplifiers therefore serve not only as buffer amplifiers but also to produce a signal at the inverting input of the the corresponding A amplifier which is of the appropriate time-coincidence and magnitude.

DC FILTERING

Figure 6A:
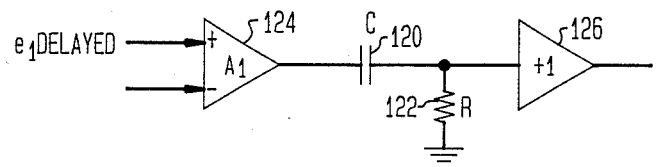

It is oftentimes necessary to remove DC components from the output signals of the various differential amplifier circuits. In the usual case, illustrated in FIG. 6A, a simple DC circuit comprised of capacitor 120 and resistor 122 is interposed between the output of amplifier 124 and a buffer 126. The problem with such a system is that it produces a high impedance output as opposed to a low impedance output.

Figure 6B:
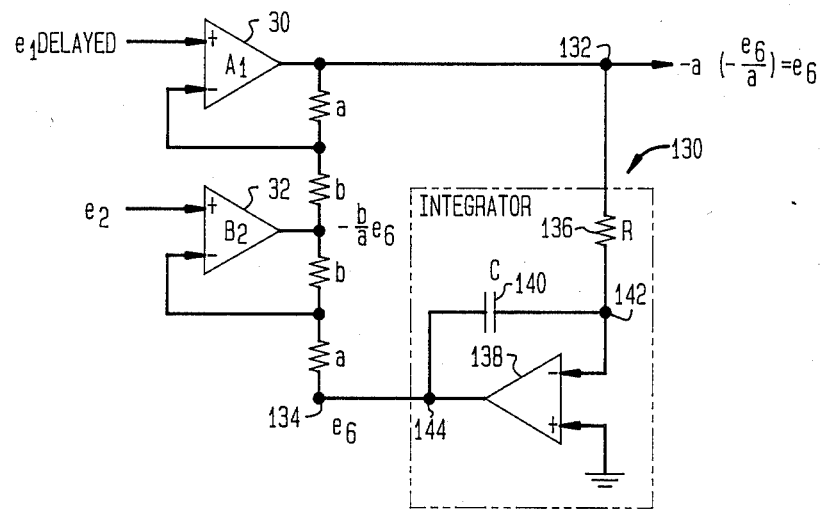

Referring to FIG. 6B, the subject differential amplifier, including the aforementioned $A_1$ amplifier 30 and the $B_2$ amplifier 32, is provided with an integrator 130 which is coupled between an output node 132 of amplifier 30 and node 134 which has previously been shown as grounded. In this case, the voltage at node 134 is designated $e_6$. Integrator 130 includes a resistor 136 which feeds the output signal at node 132 to the inverting input of an operational amplifier 138. The non-inverting input to operational amplifier 138 is grounded such that the value established at node 134 by virtue of the integrator is in fact $e_6$ which, as will be seen, is zero. Since the non-inverting input to amplifier 138 is grounded, the output through the interposition of integrator 130 is $-a(-e_6/a)$ or $e_6$. Thus, the contribution of the integrator is equal to $e_6$, which can be made to be the common reference for the system. Integrator 130 eliminates from the system all DC components without affecting the normal operation of the differential amplifier circuit which includes operational amplifiers 30 and 32. This preserves the low impedance output for amplifier 30, while at the same time, removing DC components.

The reasons that it is possible to insert the integrator come with the recognition that the previously grounded point for the $B_2$ amplifier being a voltage $e_6$ is the same voltage as the output of the integrator, assuming $e_1$ delayed and $e_2$ are zero. It will be appreciated that there are differential amplifiers where it is virtually impossible to place an integrator at the output of the differential amplifier even if buffer stages are utilized. What has therefore been provided, in addition to circuits which reduce the active components for multiple differencing, is that the circuit leads itself easily to DC filtering through the utilization of the simple expedient of an operational amplifier with an integration circuit around it, thereby providing filtered signals. What is accomplished by the above, at least for patient monitoring, is that the front ends or heads of the system can be compressed by a factor of four vis-a-vis what was possible.

Having above indicated a preferred embodiment of the present invention, it will occur to those skilled in the art that modifications and alternatives can be practiced within the spirit of the invention. It is accordingly intended to define the scope of the invention only as indicated in the following claims.

I claim:

1. Apparatus for establishing the differences between mulitple pairs of time-coincident analog input signals with a minimum number of active devices comprising:
   a bank of differential amplifier circuits limited in number to the number of pairs of signals for which the differences between pairs is sought, each of said differential amplifier circuits including a pair of first and second operational amplifiers, with each operational amplifier having high impedance inverting and non-inverting inputs and a low impedance output, the output of the second operational amplifier of a pair being connected to the inverting input of the first operational amplifier of the pair, the non-inverting inputs of said second operational amplifiers adapted to receive input signals corresponding to said analog input signals, and
   passive circuit means for coupling the output of a second operational amplifier in one pair to the respective inverting input of that second operational amplifier and for providing to the non-inverting input of a first operational amplifier of another pair of properly delayed input signal corresponding to a delayed version of the input signal applied to the non-inverting input of the second operational amplifier of said one pair, whereby a properly delayed input signal is supplied to the non-inverting input of the first operational amplifier in a differential amplifier circuit from the second operational amplifier of a different amplifier circuit without providing additional active devises.

2. The apparatus of claim 1 wherein the outputs of said differential amplifier circuits are time-coincident, thereby to permit further processing without regard to the time relationship of the output signals from said differential amplifier circuits.

3. The apparatus of claim 1 wherein said passive circuit means causes the differential amplifier circuit output signals to be both time-coincident and multiplied by the same constant.

4. The apparatus of claim 1 wherein said passive circuit means includes an attenuator circuit for each second operational amplifier coupled between the output of said second operational amplifier and an effective ground node, said attenuator circuit including series connected resistors coupled between said second operational amplifier output and said effective ground node, with the junction therebetween coupled to the inverting input of said second operational amplifier and to the non-inverting input of a first operational amplifier of another pair of operational amplifiers to provide said first operational amplifier of said other pair with a delayed signal corresponding to a delayed version of the input signal to the non-inverting input to said second operational amplifier of said first pair, whereby properly delayed input signals can be supplied to the non-inverting inputs of said differential amplifier circuits without providing additional operational amplifiers.

5. The apparatus of claim 4 wherein the weight of the resistor closest to said effective ground node is "a," and the weight of the resistor between said junction and the output of said second amplifier is "b."

6. The apparatus of claim 5 wherein each first operational amplifier includes a feedback resistor having weight "a" and wherein the first and second operational amplifiers of each pair are connected by a resistor having a weight "b" connected between the output of a corresponding second operational amplifier and the inverting input of the first operational amplifier of this corresponding pair, whereby all differential amplifier circuit outputs are time-coincident and multiplied by the same constant.

7. The apparatus of claim 4 and further including for each differential amplifier circuit high pass filter means, including an operational amplifier integrator coupled from the low impedance output node of a first operational amplifier of a pair to the effective ground node of the attenuator circuit, whereby DC components of the output of a differential amplifier are rejected without changing the low output impedance characteristic of the corresponding differential amplifier circuit.

8. The apparatus of claim 7 wherein said integrator includes an additional operational amplifier having a noninverting input coupled to ground, a low impedance output coupled to said effective ground node, a resistor connected between said low impedance output and the inverting input of said additional operational amplifier, and a capacitor coupled between said last mentioned inverting input and the output of the first operational amplifier of a pair.

9. The apparatus of claim 4 wherein selected second amplifiers of a pair include an additional attenuator circuit coupled between the associated second amplifier output and said effective ground node, wherein said analog input signals to said differential amplifier circuits include at least left arm (LA), right arm (RA), left leg (LL) and chest (C) signals from a patient being monitored, said LA, RA and LL signals having been derived from said second attenuator circuits and further including an operational amplifier having an inverting input coupled to said C signal and a non-inverting input coupled to a Wilson summing junction which sums the LA, RA and LL signals derived from said additional attenuator circuits, thereby to derive a patient monitoring voltage as the output of said further operational amplifier.

10. The apparatus of claim 9 wherein said additional attenuator circuit is identical to said first-mentioned attenuator circuit and is coupled in parallel therewith.

11. Apparatus for establishing the differences between multiple time-coincident pairs of analog input signals with a minimum number of active devices comprising:
a bank of differential amplifier circuits limited in number to the number of pairs of signals for which the differences between pairs is sought, each of said differential amplifier circuits having at least one high impedance input terminal and a low impedance output;
means within each of said differential amplifier circuits for generating a delayed version of an input signal thereto; and
means for applying said delayed version of an input signal from each differential amplifier circuit to the high impedance input terminal of another differential amplifier circuit, whereby each differential amplifier circuit is supplied with one properly delayed input signal from another differential amplifier circuit where it is subtracted from the delayed version of the input signal applied directly to this differential amplifier circuit.

12. The apparatus of claim 11 wherein said means for generating a delayed version of said input signal includes passive circuit means.

13. The apparatus of claim 12 wherein said passive circuit means includes means within each of said differential amplifier circuits for causing the outputs of all of said differential amplifier circuits to be time-coincident and for causing the outputs of all of said differential amplifier circuits to be multiplied by the same constant, whereby further processing of the output signals from said differential amplifier circuits requires no further signal conditioning.

14. The apparatus of claim 12, and further including for each differential amplifier circuit, high pass filter means, including an operational amplifier integrator coupled from the output of the corresponding differential amplifier circuit to a high impedance input terminal such that DC components of the output signal from the differential amplifier circuit are eliminated without affecting the low impedance characteristic of the output of the differential amplifier circuit.

15. The apparatus of claim 12 wherein said passive circuit means includes a voltage divider circuit, wherein its voltage dividing circuit resistive components have relative values of "a" and "b" and wherein each of said differential amplifier circuits includes first and second operational amplifiers each having inverting and noninverting inputs and an output, with said first operational amplifier having a feedback circuit from the output thereof to the inverting input thereof, which includes a resistor having a value "a" and further including a resistor interposed between the output of said second operational amplifier and the inverting input to said first operational amplifier which resistor has a value "b," said voltage dividing circuit being coupled between the output of said second operational amplifier and an effective ground node and having a junction between the elements thereof coupled to the inverting input of said second operational amplifier.

16. Apparatus for establishing the differences between multiple time-coincident pairs of analog input signals with a minimum number of active devices comprising:
a bank of differential amplifier circuits equal in number to the number of pairs of signals for which the differences between pairs is sought, each of said differential amplifier circuits having at least one high impedance input terminal and a low impedance output;
means within each of said differential amplifier circuits for generating a delayed version of an undelayed input signal applied thereto; and
means for applying said delayed version of an input signal from one differential amplifier circuit to the high impedance input terminal of another differential amplifier circuit where it is subtracted from the delayed version of an undelayed input signal applied directly to this differential amplifier circuit,
said means for generating a delayed version of said input signal having passive circuit means including a voltage divider circuit, and further including an additional voltage divider circuit connected in parallel with said first-mentioned voltage divider circuit, with said additional divider circuit having an interconnection point and means for suming the signals from selected interconnection points from selected additional voltage divider circuits so as to form a Wilson summing junction.

17. In a patient monitoring system in which electrodes are placed on a patient body and in which signals are derived from said electrodes corresponding to the signals at a left leg (LL), right leg (RL), right arm (RA), left arm (LA) and the chest (C), apparatus for establishing the differences between multiple pairs of analog input signals from said electrodes with a minimum number of active devices comprising:
a bank of differential amplifier circuits limited in number to the number of pairs of signals for which the differences between pairs is sought, each of said differential amplifier circuits including a pair of first and second operational amplifiers, with each operational amplifier having high impedance inverting and non-inverting inputs and a low impedance output, the output of the second operational amplifier of a pair being connected to the inverting input of the first operational amplifier of the pair, the non-inverting inputs of said second operational amplifiers adapted to receive input signals corresponding to said analog input signals, passive circuit means connected to the output of a second operational amplifier in one pair for providing to the non-inverting input of a first operational amplifier of another pair a properly delayed input signal corresponding to a delayed version of the input signal applied to the non-inverting input to the second operational amplifier of said one pair, said passive circuit means including an attenuator circuit for each second operational amplifier coupled between the output of said second operational amplifier and an effective ground node, said attenuator circuit including series connected resistors coupled between said second operational amplifier output and said effective ground node, with the junction therebetween coupled to the inverting input of said second operational amplifier and to the non-inverting input of a first operational amplifier of another pair of operational amplifiers to provide said first operational amplifier of said other pair with a delayed signal corresponding to a delayed version of the input signal to the non-inverting input to said second operational amplifier of said first-mentioned pair, the weight of the resistor closest to said effective ground node is "a," and the weight of the resistor between said junction and the output of said second amplifier is "b," each first operational amplifier including a feedback resistor having a weight "a," the first and second operational amplifiers being connected by a resistor having a weight "b" connected between the output of a corresponding second operational amplifier and the inverting input of the first operational amplifier of this corresponding pair, whereby said passive circuit means causes the differential amplifier circuit output signals to be both time-coincident and multiplied by the same constant, thereby to permit further processing without further signal conditioning.

18. The apparatus of claim 17 and further including for each differential amplifier circuit high pass filter means, including an operational amplifier integrator coupled from the low impedance output node of a first operational amplifier of a pair to the effective ground node of the second operational amplifier of the pair, whereby DC components of the output of a differential amplifier are rejected without changing the low output impedance characteristic of the corresponding differential amplifier circuit.

19. The apparatus of claim 18 wherein selected second amplifiers of a pair include an additional attenuator circuit coupled between the associated second amplifier output and said effective ground node, and further including an operational amplifier having an inverting input coupled to said C signal and a non-inverting input coupled to a Wilson summing junction which sums the LA, RA and LL signals derived from said additional attenuator circuits, thereby to derive a patient monitoring voltage as the output of said further operational amplifier.

* * * * *